(12) United States Patent
Büsing et al.

(10) Patent No.: US 7,947,382 B2
(45) Date of Patent: *May 24, 2011

(54) ELECTROLUMINESCENT POLYMERS AND THE USE THEREOF

(75) Inventors: Arne Büsing, Frankfurt (DE); Susanne Heun, Bad Soden (DE); Silke Türk, Montabaur (DE); Corinna Leske, Frankfurt (DE)

(73) Assignee: Merck Patent GmbH (DE)

( * ) Notice: Subject to any disclaimer, the term of this patent is extended or adjusted under 35 U.S.C. 154(b) by 589 days.

This patent is subject to a terminal disclaimer.

(21) Appl. No.: 11/578,540

(22) PCT Filed: Apr. 26, 2005

(86) PCT No.: PCT/EP2005/004448
§ 371 (c)(1),
(2), (4) Date: Oct. 16, 2006

(87) PCT Pub. No.: WO2005/104264
PCT Pub. Date: Nov. 3, 2005

(65) Prior Publication Data
US 2007/0205714 A1    Sep. 6, 2007

(30) Foreign Application Priority Data
Apr. 26, 2004 (DE) .......................... 10 2004 020 298

(51) Int. Cl.
*B32B 9/00* (2006.01)
(52) U.S. Cl. ........................................ 428/690; 428/624
(58) Field of Classification Search ................... 528/398
See application file for complete search history.

(56) References Cited

U.S. PATENT DOCUMENTS

| | | | |
|---|---|---|---|
| 4,833,410 A | 5/1989 | Briguet et al. | |
| 5,792,568 A * | 8/1998 | Emoto et al. ................ | 428/690 |
| 6,285,188 B1 | 9/2001 | Sakakura | |
| 6,479,998 B1 | 11/2002 | Yui et al. | |
| 6,493,572 B1 | 12/2002 | Su et al. | |
| 6,506,504 B1 * | 1/2003 | Kwon et al. ................ | 428/690 |
| 6,956,095 B2 | 10/2005 | Treacher et al. | |
| 6,958,608 B2 | 10/2005 | Takagi et al. | |
| 6,994,893 B2 | 2/2006 | Spreitzer et al. | |
| 7,094,897 B2 | 8/2006 | Stossel et al. | |
| 2004/0135131 A1 | 7/2004 | Treacher et al. | |
| 2004/0138455 A1 | 7/2004 | Stossel et al. | |
| 2004/0206939 A1 | 10/2004 | Spreitzer et al. | |
| 2005/0038223 A1 | 2/2005 | Becker et al. | |
| 2006/0058494 A1 | 3/2006 | Busing et al. | |
| 2006/0127696 A1 | 6/2006 | Stossel et al. | |
| 2006/0149022 A1 | 7/2006 | Parham et al. | |
| 2006/0199943 A1 * | 9/2006 | Falcou et al. ................ | 528/422 |

FOREIGN PATENT DOCUMENTS

| | | |
|---|---|---|
| DE | 103 43 606 | 4/2005 |
| DE | 103 49 033 | 5/2005 |
| DE | 103 50 606 | 6/2005 |
| EP | 1 239 526 | 9/2002 |
| EP | 1 329 474 | 7/2003 |
| JP | 2003055276 * | 2/2003 |
| WO | WO-90/13148 | 11/1990 |
| WO | WO 9621559 * | 7/1996 |
| WO | WO-00/46321 | 8/2000 |
| WO | WO-02/068435 | 9/2002 |
| WO | WO-02/072714 | 9/2002 |
| WO | WO-02/077060 | 10/2002 |
| WO | WO-02/081488 | 10/2002 |
| WO | WO-03/019694 | 3/2003 |
| WO | WO-03/020790 | 3/2003 |
| WO | WO-03/048225 | 6/2003 |
| WO | WO-2004/026886 | 4/2004 |
| WO | WO-2004/037887 | 5/2004 |
| WO | WO-2004/070772 | 8/2004 |
| WO | WO-2004/113468 | 12/2004 |
| WO | WO-2005/014688 | 2/2005 |
| WO | WO-2005/014689 | 2/2005 |

OTHER PUBLICATIONS

PCT International Search Report and Written Opinion for International Application No. PCT/US04/37054 filed Nov. 5, 2004.
Brown, W. G. et al., "Conversion of 2,7-Dibromofluorene to 2, 7-Dibromophenanthrene", Journal of the American Chemical Society 65 (1943), pp. 1235-1236.
Bochenkov, V. N., "Synthesis of Some 2,7- and 2,5-Disubstituted Phenanthrenes", Journal of Organic Chemistry of the USSR 12 (1976), pp. 2355-2357.
Washburn, L. C. et al., "Potential Antimalarials. 8. Some 10-Substituted 9-Phenanthrenemethanols", Journal of Medicinal Chemistry 17(7) (1974), pp. 676-682.
Bradsher, C. K. et al., "Aromatic Cyclodehydration. XXXIII. 2, 7-Disubstituted Phenanthrenes", Journal of the American Chemical Society 78 (1956), pp. 3196-3198.

* cited by examiner

*Primary Examiner* — Randy Gulakowski
*Assistant Examiner* — Shane Fang
(74) *Attorney, Agent, or Firm* — Connolly Bove Lodge & Hutz LLP

(57) ABSTRACT

The present invention relates to polymers which contain novel structural units of the formula (I). The materials according to the invention exhibit improved efficiency and a longer lifetime on use in a polymeric organic light-emitting diode.

34 Claims, No Drawings

ELECTROLUMINESCENT POLYMERS AND THE USE THEREOF

RELATED APPLICATIONS

This application is a national stage application (under 35 U.S.C. 371) of PCT/EP2005/004448 filed Apr. 26, 2005, which claims benefit of German application 10 2004 020 298.2 filed Apr. 26, 2004.

Broadly based research on the commercialization of display and illumination elements based on polymeric (organic) light-emitting diodes (PLEDs) has been carried out for about 13 years. This development was initiated by the fundamental developments disclosed in WO 90/13148. A first, albeit simple, product (a small display in a razor from PHILIPS N.V.) has been available on the market for a short time. However, significant improvements in the materials used are still necessary in order to make these displays a true competitor to the liquid-crystal displays (LCDs) which currently dominate the market.

For the production of all three emission colours, it is necessary to copolymerise certain comonomers into the corresponding polymers (cf., for example, WO 00/46321, WO 03/020790 and WO 02/077060). Thus, starting from a blue-emitting basic polymer ("back-bone"), it is then generally possible to produce the two other primary colours red and green.

Various classes of material have already been proposed or developed as polymers for full-colour display elements. Thus, polyfluorene derivatives come into consideration; furthermore, polyspirobifluorene, polydihydrophenanthrene and polyindenofluorene derivatives are also a possibility. Polymers which contain a combination of the two first-mentioned structural elements have also already been proposed. In general, polymers which contain poly-paraphenylene (PPP) as structural element are possible for such use.

The polymers in accordance with the prior art in some cases already exhibit good properties in use in PLEDs. In spite of the advances that have already been achieved, however, these polymers still do not meet the requirements made of them for high-quality applications. In particular, the lifetime of the green- and especially the blue-emitting polymers is still inadequate for many applications, as is the efficiency of the red-emitting polymers. Furthermore, the emission colour in many polymers blue-emitting in accordance with the prior art is still not sufficiently deep blue.

Surprisingly, it has now been found that a novel class of polymers has very good properties which surpass the above-mentioned prior art. The present invention therefore relates to these polymers and to the use thereof in PLEDs. The novel structural units are particularly suitable as polymer backbone, but also as hole conductors, electron conductors or emitters, depending on the substitution pattern.

The use of phenanthrenes in electroluminescent polymers has already occasionally been mentioned in general terms, for example in WO 02/077060, WO 03/020790 and WO 05/014689. However, it is only listed in general terms therein that these structural elements, like a large multiplicity of further monomers, may be present as possible further elements in addition to the actual polymer backbone. Particular advantages of these units are not described. In addition, it is only described in very general terms that these may be substituted by non-aromatic substituents or unsubstituted. However, the use of unsubstituted phenanthrene units results in insoluble polymers, and consequently these units can be used at most in a very small proportion. However, which substituents are particularly suitable and in which positions of the phenanthrene unit these substituents should preferably be bonded is not evident from these descriptions. It is just as little evident therefrom that the novel structural units are particularly suitable for being employed in a higher proportion in the polymer since in the prior art they are only mentioned as comonomers in relatively small proportions. It is thus also not evident to the person skilled in the art how these units could beneficially be used in electroluminescent polymers. The general mention of unsubstituted phenanthrene units or phenanthrene units which are substituted as desired should therefore be regarded as a chance disclosure.

Substitution of the phenanthrene units in the 9- or 9,10-position and the linking in the 2,7-position in the polymer has, surprisingly, proven particularly suitable in comparison with substitution in other positions of the phenanthrene unit. This preference can be explained by the particularly good synthetic accessibility of the units substituted in these positions, but also by the better optical and electronic properties.

The invention relates to polymers containing at least 5 mol %, preferably at least 10 mol %, particularly preferably at least 30 mol %, very particularly preferably at least 50 mol %, of units of the formula (1)

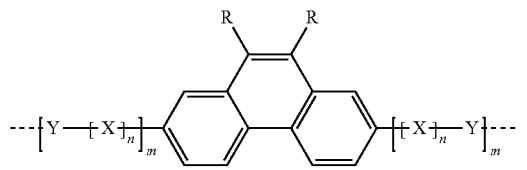

Formel (1)

where the symbols and indices used have the following meaning:

R is on each occurrence, identically or differently, H, a straight-chain, branched or cyclic alkyl chain having 1 to 40 C atoms, which may be substituted by $R^1$, and in which, in addition, one or more non-adjacent C atoms may be replaced by $N-R^1$, O, S, O—CO—O, CO—O, $-CR^1=CR^1-$ or $-C\equiv C-$, with the proviso that the heteroatoms are not bonded directly to the phenanthrene unit, and in which, in addition, one or more H atoms may be replaced by F, Cl, Br, I or CN, or an aromatic or heteroaromatic ring system having 2 to 40 C atoms, which may be substituted by one or more radicals $R^1$, or a combination of a plurality of these systems; the two radicals R here may also form a further mono- or polycyclic, aliphatic ring system with one another; with the proviso that at least one of the two radicals R is not equal to H;

X is on each occurrence, identically or differently, $-CR^1=CR^1-$, $-C\equiv C-$ or N—Ar;

Y is on each occurrence, identically or differently, a divalent aromatic or heteroaromatic ring system having 2 to 40 C atoms, which may be substituted by one or more radicals $R^1$ or unsubstituted;

$R^1$ is on each occurrence, identically or differently, H, a straight-chain, branched or cyclic aakyl or alkoxy chain having 1 to 22 C atoms, in which, in addition, one or more non-adjacent C atoms may be replaced by $N-R^2$, O, S, O—CO—O, CO—O, $-CR^2=CR^2-$, $-C\equiv C-$ and in which, in addition, one or more H atoms may be replaced by F, Cl, Br, I or CN, or an aryl, heteroaryl, aryloxy or heteroaryloxy group having 5 to 40 C atoms, which may also be substituted by one or more non-aromatic radicals $R^1$; two or more of the radicals $R^1$ here may also form a ring system with one another and/or with R; or F, Cl, Br, I, CN, $N(R^2)_2$, $Si(R^2)_3$ or $B(R^2)_2$;

$R^2$ is on each occurrence, identically or differently, H or an aliphatic or aromatic hydro-carbon radical having 1 to 20 C atoms;

Ar is on each occurrence, identically or differently, a monovalent aromatic or heteroaromatic ring system having 2 to 40 C atoms, which may be substituted by $R^1$ or unsubstituted;

n is on each occurrence, identically or differently, 0 or 1;

m is on each occurrence, identically or differently, 0, 1 or 2;

the dashed bond in formula (1) here as in all other formulae denotes the link in the polymer; it is not intended to represent a methyl group here.

Although this is evident from the description, it should again be explicitly pointed out here that the structural units of the formula (1) may be asymmetrically substituted, i.e. that different substituents R or $R^1$ may be present on a unit, or that the substituents X and Y, if present, are different or only occur on one side.

For the purposes of this invention, an aromatic or heteroaromatic ring system is intended to be taken to mean a system which does not necessarily contain only aromatic or heteroaromatic groups, but instead in which a plurality of aromatic or heteroaromatic groups may also be interrupted by a short non-aromatic unit (<10% of the atoms other than H, preferably <5% of the atoms other than H), such as, for example, $sp^3$-hybridised C, O, N, etc. Thus, for example, systems such as 9,9'-spirobifluorene, 9,9-diarylfluorene, triarylamine, etc., are thus also intended to be understood as aromatic ring systems. An aromatic ring system here contains at least 6 C atoms and a heteroaromatic ring system contains at least 2 C atoms and at least one heteroatom, preferably selected from N, O and/or S, with the proviso that the sum of C atoms and heteroatoms gives at least 5.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methyl-butoxy. A $C_2$-$C_{24}$ aryl or heteroaryl group, which may be monovalent or divalent depending on the use, which may in each case also be substituted by the above-mentioned radicals $R^1$ and which may be linked to the aromatic or heteroaromatic radical via any desired positions, is taken to mean, in particular, groups which are derived from benzene, naphthalene, anthracene, phenanthrene, pyrene, chrysene, perylene, fluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazineimidazole, quinoxalineimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. Aromatic ring systems are furthermore taken to mean, in particular, biphenylene, terphenylene, fluorene, spirobifluorene, dihydrophenanthrene, dihydropyrene, tetrahydropyrene or cis- or trans-indenofluorene.

One aspect of the invention relates to conjugated polymers. A further aspect of the invention relates to non-conjugated polymers. A still further aspect of the invention relates to partially conjugated polymers. Preference is given to conjugated or partially conjugated polymers.

For the purposes of this invention, conjugated polymers are polymers which contain in the main chain principally $sp^2$-hybridised carbon atoms, which may also be replaced by corresponding heteroatoms. In the simplest case, this means the alternating presence of double and single bonds in the main chain. Principally means that naturally occurring defects which result in conjugation interruptions do not devalue the term "conjugated polymer". Furthermore, the term conjugated is likewise used in this application text if, for example, arylamine units and/or certain heterocycles (i.e. conjugation via N, O or S atoms) and/or organometallic complexes (i.e. conjugation via the metal atom) are present in the main chain. By contrast, units such as, for example, simple alkyl bridges, (thio)ether, ester, amide or imide links would clearly be defined as non-conjugated segments. A partially conjugated polymer is intended to be taken to mean a polymer in which relatively long conjugated sections in the main chain are interrupted by non-conjugated sections, or which contains relatively long conjugated sections in the side chains of a polymer which is non-conjugated in the main chain.

Besides units of the formula (1), the polymers according to the invention may also contain further structural elements. These are, inter alia, those as disclosed and extensively listed in WO 02/077060 and WO 05/014689. The further structural units may originate, for example, from the classes described below:

Group 1: Units which increase the hole-injection and/or -transport properties of the polymers;

Group 2: Units which increase the electron-injection and/or -transport properties of the polymers;

Group 3: Units which have combinations of individual units from group 1 and group 2;

Group 4: Units which change the emission characteristics to such an extent that electrophosphorescence instead of electrofluorescence may be obtained;

Group 5: Units which improve the transition from the singlet state to the triplet state;

Group 6: Units which influence the morphology or also the emission colour of the resultant polymers;

Group 7: Units which are typically used as backbone.

Preferred polymers according to the invention are those in which at least one structural element has charge-transport properties, i.e. which contain units from groups 1 and/or 2.

Structural elements from group 1, which have hole-transport properties, are, for example, triarylamine, benzidine, tetraaryl-para-phenylenediamine, triarylphosphine, phenothiazine, phenoxazine, dihydrophenazine, thianthrene, dibenzo-p-dioxin, phenoxathiyne, carbazole, azulene, thiophene, pyrrole and furan derivatives and further O—, S— or N-containing heterocycles having a high HOMO (HOMO=highest occupied molecular orbital); these arylamines and heterocycles preferably result in an HOMO in the polymer of greater than −5.8 eV (against vacuum level), particularly preferably of greater than −5.5 eV.

Structural elements from group 2, which have electron-transport properties, are, for example, pyridine, pyrimidine, pyridazine, pyrazine, oxadiazole, quinoline, quinoxaline, benzothiadiazole and phenazine derivatives, but also tri-arylboranes and further O—, S— or N-containing heterocycles having a low LUMO (LUMO=lowest unoccupied molecular orbital); these units preferably result in an LUMO in the polymer of less than −2.7 eV (against vacuum level), particularly preferably of less than −3.0 eV.

It may be preferred for the polymers according to the invention to contain units from group 3 in which structures which increase the hole mobility and which increase the electron mobility (i.e. units from group 1 and 2) are bonded directly to one another. Some of these units may serve as emitters and shift the emission colour into the green, yellow or red; their use is thus suitable, for example, for the production of other emission colours from originally blue-emitting polymers.

Structural units in accordance with group 4 are those which are able to emit light from the triplet state with high efficiency even at room temperature, i.e. exhibit electrophosphorescence instead of electrofluorescence, which frequently effects an increase in the energy efficiency. Suitable for this purpose are firstly compounds which contain heavy atoms having an atomic number of greater than 36. Particularly suitable are compounds which contain d or f transition metals which satisfy the above-mentioned condition. Very particular preference is given here to corresponding structural units which contain elements from group 8 to 10 (Ru, Os, Rh, Ir, Pd, Pt). Suitable structural units for the polymers according to the invention here are, for example, various complexes which are described, for example, in the application specifications WO 02/068435, WO 02/081488, EP 1239526 and WO 04/026886. Corresponding monomers are described in WO 02/068435 and in the unpublished application DE 10350606.3.

Structural elements from group 5 are those which improve the transition from the singlet state to the triplet state and which, employed in support of the structural elements from group 4, improve the phosphorescence properties of these structural elements. Particularly suitable for this purpose are carbazole and bridged carbazole dimer units, as described in WO 04/070772 and WO 04/113468. Also suitable for this purpose are ketones, phosphine oxides, sulfoxides and similar compounds, as described in the unpublished application DE 10349033.7.

Structural elements from group 6 which influence the morphology or also the emission colour of the polymers are, besides those mentioned above, those which have at least one further aromatic or another conjugated structure which does not fall under the above-mentioned groups, i.e. which has only little effect on the charge-carrier mobility, which are not organometallic complexes or which have no influence on the singlet-triplet transition. Structural elements of this type may influence the morphology, but also the emission colour of the resultant polymers. Depending on the unit, they can therefore also be employed as emitters. Preference is given here to aromatic structures having 6 to 40 C atoms or also tolan, stilbene or bisstyrylarylene derivatives, each of which may be substituted by one or more radicals $R^1$. Particular preference is given here to the incorporation of 1,4-phenylene, 1,4-naphthylene, 1,4- or 9,10-anthrylene, 1,6- or 2,7- or 4,9-pyrenylene, 3,9- or 3,10-perylenylene, 4,4'-biphenylylene, 4,4"-terphenylylene, 4,4'-bi-1,1'-naphthylylene, 4,4'-tolanylene, 4,4'-stilbenylene or 4,4"-bisstyrylarylene derivatives.

Structural elements from group 7 are units which contain aromatic structures having 6 to 40 C atoms, which are typically used as polymer backbone. These are, for example, 4,5-di-hydropyrene derivatives, 4,5,9,10-tetrahydropyrene derivatives, fluorene derivatives, 9,9'-spirobifluorene derivatives, 9,10-dihydrophenanthrene derivatives, 5,7-dihydrodibenzooxe-pine derivatives and cis- and trans-indenofluorene derivatives. However, since the proportion of units of the formula (1) is very particularly preferably at least 50 mol %, these structural elements are not preferably used here as the principal polymer backbone.

Preference is given to polymers according to the invention which, besides structural units of the formula (1), simultaneously additionally contain one or more units selected from groups 1 to 7. It may likewise be preferred for more than one structural unit from a group to be present simultaneously.

The proportion of the units of the formula (1) is preferably at least 10 mol %, particularly preferably at least 30 mol %, very particularly preferably at least 50 mol %. This preference applies in particular if the units of the formula (1) are the polymer backbone. In the case of other functions, other proportions may be preferred, for example a proportion in the order of 5 to 20 mol % in the case of the hole conductor or the emitter in an electroluminescent polymer. For other applications, for example for organic transistors, the preferred proportion may again be different, for example up to 100 mol % in the case of hole- or electron-conducting units.

Preference is given to polymers according to the invention which, in addition to structural units of the formula (1), also contain at least one structural unit from the above-mentioned groups. Particular preference is given to at least two structural units from different classes of those mentioned above. Very particularly preferably, one of these structural units is selected from the group of the hole-conducting units and the other group is an emitting unit, where these two functions (hole conduction and emission) may also be taken on by the same unit.

Units of the formula (1) are also particularly suitable for the synthesis of white-emitting copolymers. These preferably contain a sufficiently small proportion of green- and red-emitting units, resulting overall in white emission. The way in which white-emitting copolymers can be synthesised is described in detail in the unpublished application DE 10343606.5.

The polymers according to the invention preferably have 10 to 10,000, particularly preferably 50 to 5000, very particularly preferably 50 to 2000, recurring units.

The requisite solubility of the polymers is ensured, in particular, by the substituents R or $R^1$ on the units of the formula (1) and optionally on further units present. If further substituents are present, these also contribute to the solubility.

In order to ensure adequate solubility, it is preferred for on average at least 2 non-aromatic C atoms to be present in the substituents per recurring unit. Preference is given here to at least 4, particularly preferably at least 6, C atoms. Some of these C atoms may also be replaced by O or S. However, it is entirely possible for this to mean that a certain proportion of recurring units does not carry any further non-aromatic substituents.

In order to avoid impairing the morphology of the film, it is preferred to have no long-chain substituents having more than 12 C atoms in a linear chain, preferably none having more than 8 C atoms, particularly preferably none having more than 6 C atoms. Non-aromatic C atoms are, as, for example, in the description of R and $R^1$ in formula (1), present in corresponding straight-chain, branched or cyclic alkyl or alkoxy chains.

Preference is given to polymers according to the invention in which the symbol R, identically or differently on each occurrence, stands for a straight-chain, branched or cyclic alkyl chain having 2 to 15 C atoms, in which, in addition, one or more non-adjacent C atoms may be replaced by N—$R^1$, O, S, O—CO—O, CO—O, —CH═CH— or —C≡C—, with the proviso that the heteroatoms are not bonded directly to the phenanthrene unit, and in which, in addition, one or more H atoms may be replaced by F or CN, or an aromatic or heteroaromatic group having 4 to 20 C atoms, which may also be substituted by one or more non-aromatic radicals $R^1$, or a combination of a plurality of these systems. The two radicals R here may together also form a further mono- or polycyclic, aliphatic ring system. R, identically or differently on each occurrence, particularly preferably stands for a straight-chain, branched or cyclic alkyl chain having 4 to 8 C atoms, particularly preferably a branched alkyl chain, in which, in addition, one or more non-adjacent C atoms may be replaced by N—$R^1$, O, S, —$CR^1$═$CR^1$— or —C≡C—, with the proviso that these are not directly adjacent to the phenanthrene unit, and in which, in addition, one or more H atoms may be replaced by F, or an aryl or heteroaryl group having 5 to 10 C atoms, which may be substituted by $R^1$ or unsubstituted; the two radicals R here may together also form a further mono- or polycyclic ring system.

Preference is furthermore given to polymers according to the invention in which the symbol X, identically or differently on each occurrence, stands for —CH═Ch—, —C≡C— or N—Ar.

Preference is furthermore given to polymers according to the invention in which the symbol Y, identically or differently on each occurrence, stands for a divalent aromatic or heteroaromatic ring system having 4 to 25 C atoms, which may be substituted by one or more radicals $R^1$. Y, identically or differently on each occurrence, particularly preferably stands for a divalent aromatic or heteroaromatic ring system having 6 to 16 C atoms or spirobifluorene, each of which may be substituted by one or more non-aromatic radicals $R^1$.

Preference is furthermore given to polymers according to the invention in which the symbol Ar, identically or differently on each occurrence, stands for a monovalent aromatic or heteroaromatic ring system having 4 to 25 C atoms, which may be substituted by $R^1$ or unsubstituted. Ar, identically or differently on each occurrence, particularly preferably stands for a monovalent aryl or heteroaryl group having 4 to 16 C atoms, which may be substituted by non-aromatic radicals $R^1$.

Preference is furthermore given to polymers according to the invention in which the index m, identically or differently on each occurrence, is 0 or 1.

Depending on the substitution pattern, the units of the formula (1) are suitable for various functions in the polymer. Thus, they can preferably be employed as (electron-conducting) polymer backbone, as hole conductor or as emitter. Which compounds are particularly suitable for which function is described, in particular, by the substituents X and Y. The substituents R also have an effect on the electronic properties of the units of the formula (1).

Thus, the following preferably applies to the use as polymer backbone:
n is on each occurrence equal to 0,
i.e. it is a purely aromatic structural unit.

The following preferably applies to the use of units of the formula (1) as hole-transporting units:

n is on each occurrence, identically or differently, 0 or 1, where at least one n=1;

m is on each occurrence, identically or differently, 0, 1 or 2, where m is not equal to 0 if the corresponding n=1;

X is on each occurrence N—Ar;

i.e. they are triarylamine derivatives of phenanthrene.

Furthermore, it is also possible to use units of the formula (1) as hole-transporting units if the index n=0, if at least one of the radicals R (or radicals $R^1$ bonded to R) contain at least one diarylamine group.

The following preferably applies to the use of units of the formula (1) as emitters:

n is on each occurrence, identically or differently, 0 or 1, where at least one n=1;

m is on each occurrence, identically or differently, 0, 1 or 2, where m is not equal to 0 if the corresponding n=1;

X is on each occurrence, identically or differently, —$CR^1$═$CR^1$—, —C≡C— or N—Ar, where at least one X is equal to —$CR^1$═$CR^1$— or —C≡C—, i.e. they are diarylvinylene or diarylacetylene derivatives in the broadest sense, which may also additionally contain triarylamine units.

Furthermore, it is also possible to use units of the formula (1) as emitting units if the index n=0, if at least one of the radicals R (or radicals $R^1$ bonded to R) contain at least one diarylvinylene or diarylacetylene group.

Preference is furthermore given to units of the formula (1) which are symmetrically substituted in the 9,10-positions of the phenanthrene units. This preference can be explained by the better synthetic accessibility of the monomers. It is thus preferred for all R in a unit of the formula (1) to be identical and particularly preferably also identically substituted. This preference does not exclude the substituents X and Y from occurring on only one side or also being different.

Examples of preferred units of the formula (1) are structures in accordance with Examples 1 to 36 shown, where the link in the polymer in each case takes place through the 2,7-positions of the phenanthrene units, as indicated via the dashed bonds. Possible substituents on the groups R are generally not shown for better clarity. Alkyl here generally stands for an aliphatic alkyl group, aryl for an aromatic or heteroaromatic system, as described for R. Examples 1 to 21 here are examples of backbone units, Examples 22 to 33 are examples of emitting units and Examples 34 to 36 are examples of hole-conducting units.

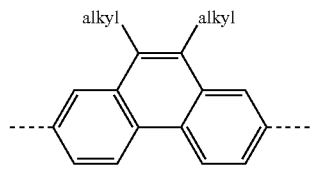

Example 1

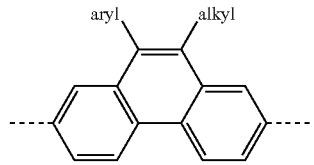

Example 2

-continued
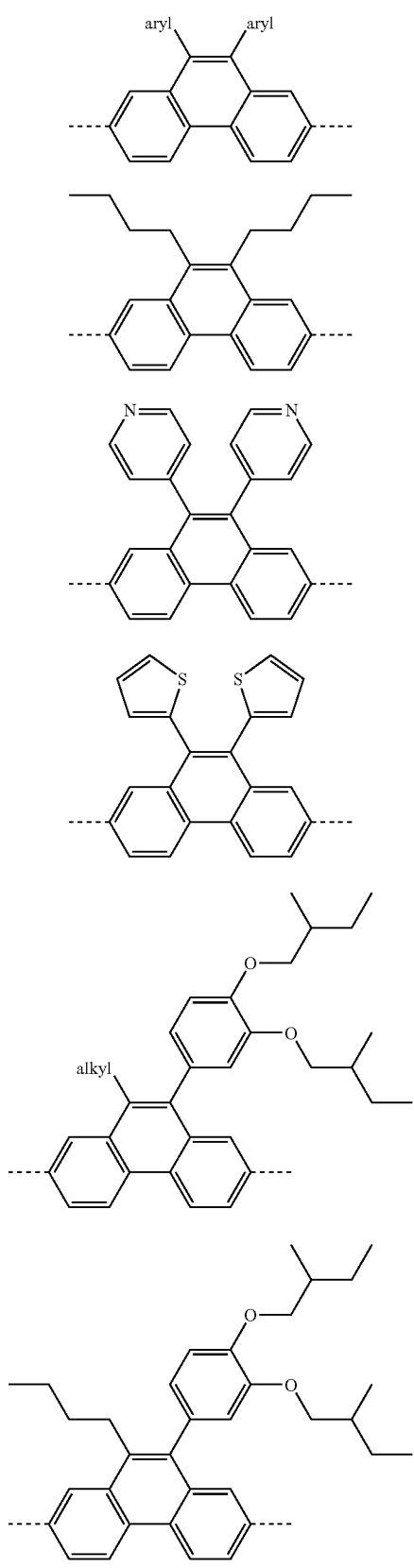
-continued
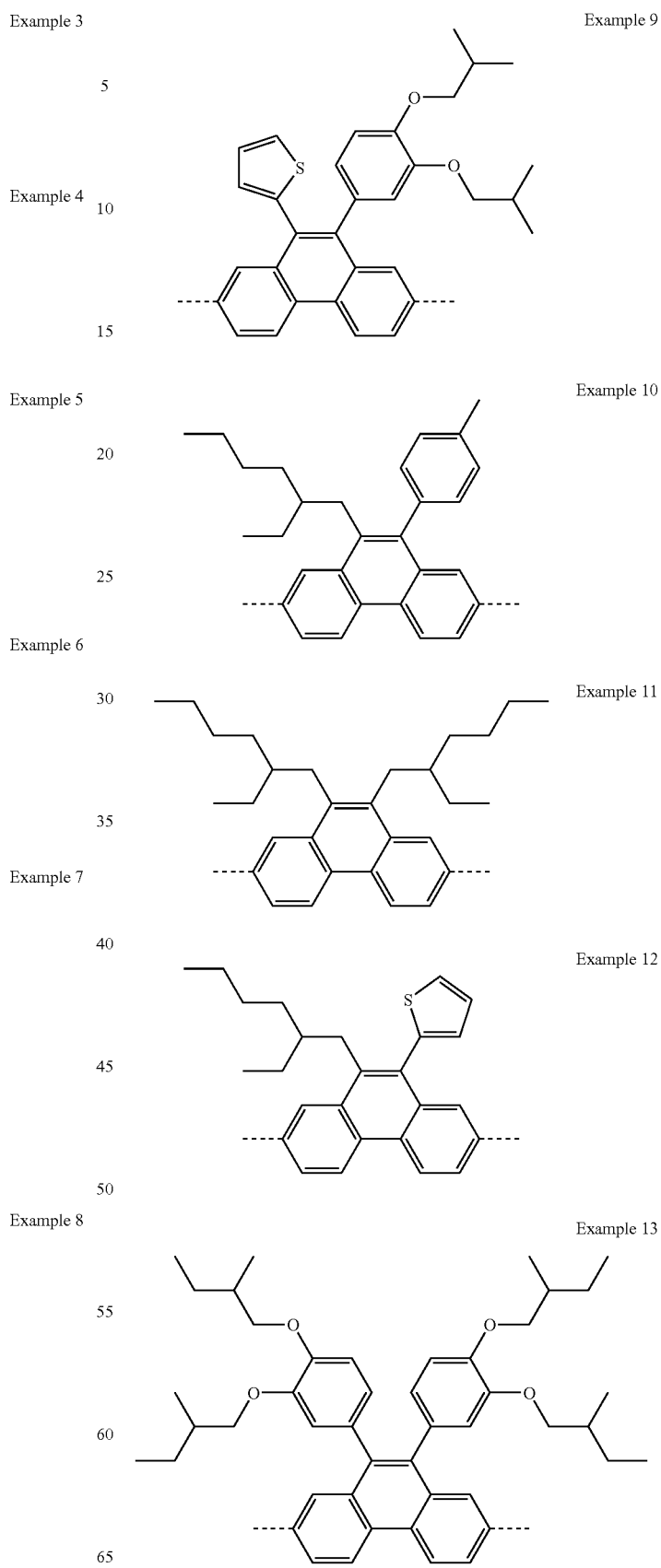

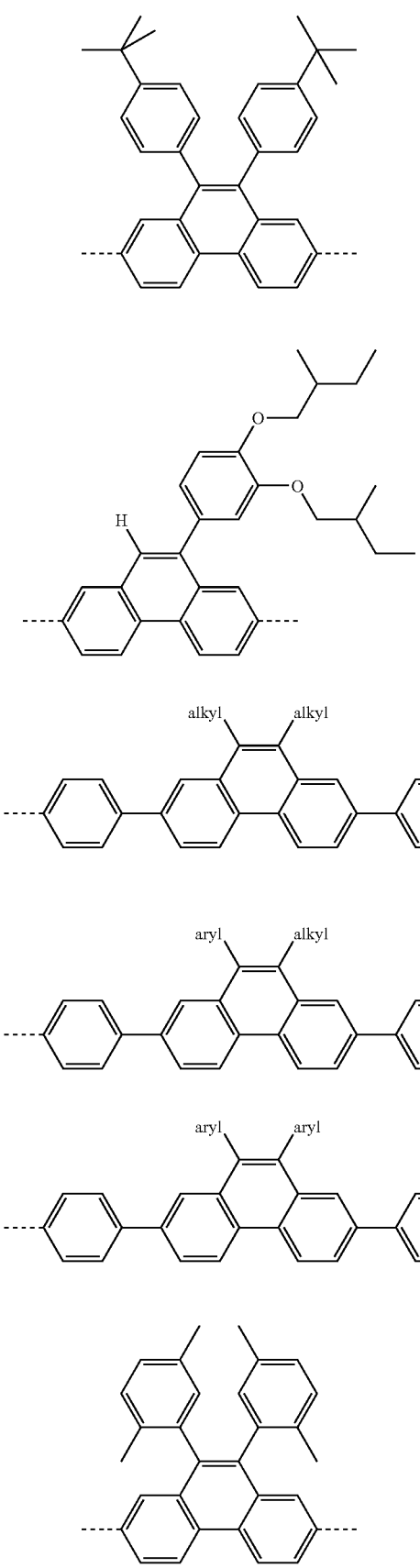
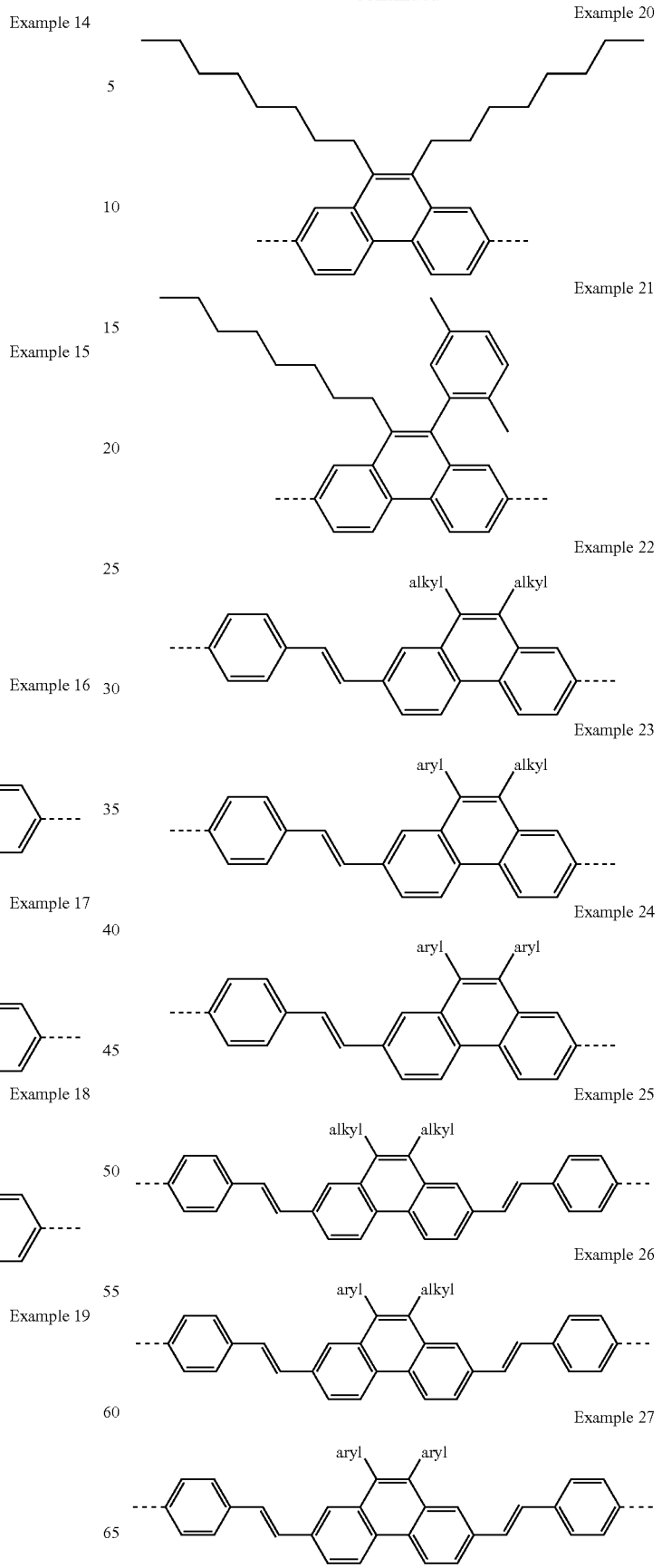

Example 28
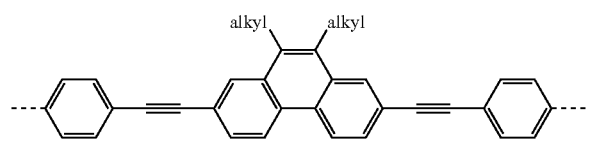

Example 29
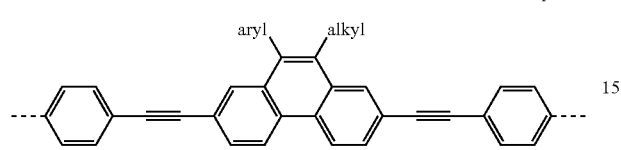

Example 30
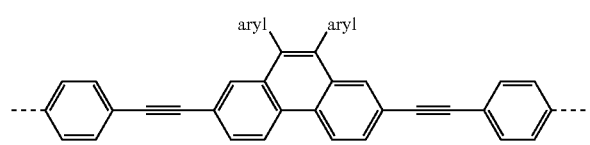

Example 31
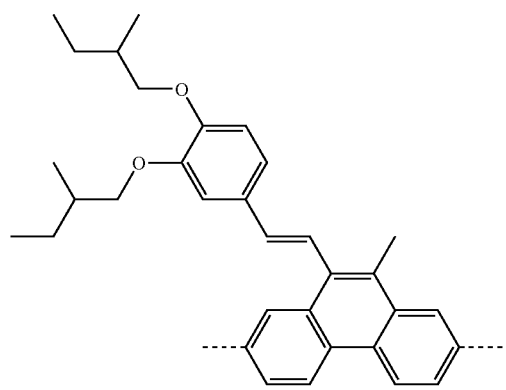

Example 32
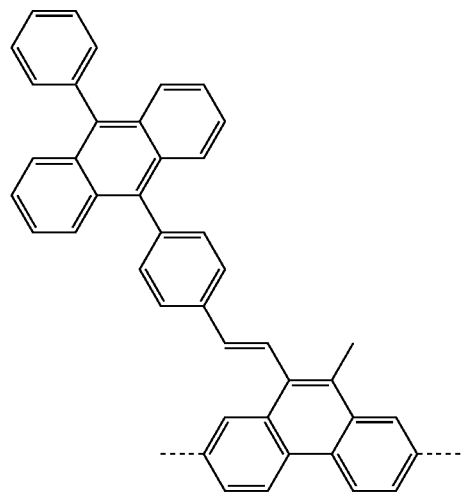

Example 33
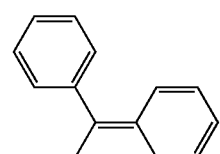

Example 34
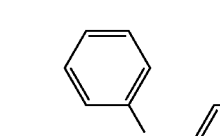

Example 35
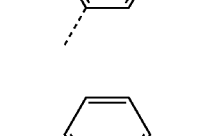

Example 36
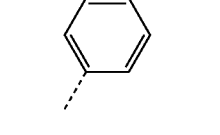

The polymers according to the invention are homopolymers or copolymers. Besides one or more structures of the formula (1), copolymers according to the invention may potentially have one or more further structures, preferably from the above-mentioned groups 1 to 7.

The copolymers according to the invention can have random, alternating or block-like structures or also have a plurality of these structures alternating. The way in which copolymers having block-like structures can be obtained is described in detail, for example, in WO 05/014688.

Use of a plurality of different structural elements enables properties, such as solubility, solid-phase morphology, colour, charge-injection and -transport properties, temperature stability, electro-optical characteristics, etc., to be adjusted.

The polymers according to the invention are prepared by polymerisation of one or more types of monomer, at least one monomer of which results in units of the formula (1) in the polymer. There are in principle many corresponding polymerisation reactions. However, a few types which result in C—C or in C—N links have proven particularly successful here:
(A) SUZUKI polymerisation;
(B) YAMAMOTO polymerisation;
(C) STILLE polymerisation;
(D) HARTWIG-BUCHWALD polymerisation.

The way in which the polymerisation can be carried out by these methods and the way in which the polymers can be separated off from the reaction medium and purified is described in detail in WO 04/037887.

Monomers which result in structural units of the formula (1) in polymers according to the invention are phenanthrene derivatives which are suitably substituted in the 9- and/or 10-position and have suitable functionalities in the 2,7-position (or in a suitable position on Y, if present) which allow this monomer unit to be incorporated into the polymer. These monomers are novel and are therefore likewise a subject-matter of the present invention.

The invention furthermore relates to bifunctional monomeric compounds of the formula (2)

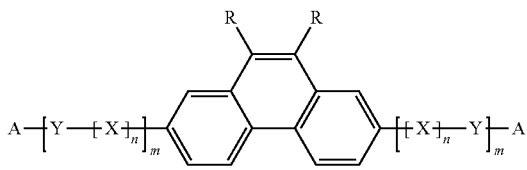

Formula (2)

characterized in that the two functional groups A, identically or differently, copolymerise under conditions of C—C or C—N linking reaction; the other symbols and indices have the same meaning as in formula (1).

A is preferably selected from Cl, Br, I, O-tosylate, O-triflate, $O—SO_2R^2$, $B(OR^2)_2$ and $Sn(R^2)_3$, particularly preferably from Br, I and $B(OR^2)_2$, where $R^2$ has the same meaning as described above, and where two or more radicals $R^2$ may also form a ring system with one another.

The C—C linking reactions are preferably selected from the groups of the SUZUKI coupling, the YAMAMOTO coupling and the STILLE coupling; the C—N linking reaction is preferably a HARTWIG-BUCHWALD coupling.

The same preference as described above for structural units of the formula (1) applies to bifunctional monomeric compounds of the formula (2).

It may be preferred to use the polymer according to the invention not as the pure substance, but instead as a mixture (blend) together with any desired further polymeric, oligomeric, dendritic or low-molecular-weight substances. These can improve, for example, the electronic properties, influence the transfer from the singlet state to the triplet state or themselves emit light from the singlet or triplet state. However, electronically inert substances may also be appropriate in order, for example, to influence the morphology of the polymer film formed or the viscosity of polymer solutions. The present invention therefore also relates to blends of this type.

The invention furthermore relates to solutions and formulations of one or more polymers or blends according to the invention in one or more solvents. The way in which polymer solutions can be prepared is described, for example, in WO 02/072714, in WO 03/019694 and in the literature cited therein. These solutions can be used in order to produce thin polymer layers, for example by surface-coating methods (for example spin coating) or printing methods (for example ink-jet printing).

The polymers according to the invention can be used in PLEDs. These contain cathode, anode, emission layer and optionally further layers, such as, for example, preferably a hole-injection layer and optionally an interlayer between the hole-injection layer and the emission layer. The way in which PLEDs can be produced is described in detail as a general process in WO 04/037887, which should be adapted correspondingly for the individual case. As described above, the polymers according to the invention are very particularly suitable as electroluminescent materials in the PLEDs or displays produced in this way.

For the purposes of the invention, electroluminescent materials are regarded as being materials which can be used as active layer in a PLED. Active layer means that the layer is capable of emitting light on application of an electric field (light-emitting layer) and/or that it improves the injection and/or transport of the positive and/or negative charges (charge-injection or charge-transport layer). It may also be an interlayer between a hole-injection layer and an emission layer.

The invention therefore also relates to the use of a polymer according to the invention in a PLED, in particular as electroluminescent material.

The invention thus likewise relates to a PLED having one or more active layers, where at least one of these active layers comprises one or more polymers according to the invention. The active layer can be, for example, a light-emitting layer and/or a transport layer and/or a charge-injection layer and/or an interlayer.

The polymers according to the invention have the following surprising advantages over the polyspirobifluorenes described in WO 03/020790 and polyfluorenes described in WO 02/077060, which are hereby cited as closest prior art:
(1) It has been found that the polymers according to the invention (with otherwise identical or similar composition) have higher luminous efficiencies in use. This applies particularly to the copolymers which exhibit blue emission. This is of enormous importance since either the same brightness can be achieved therewith at the same time as lower energy consumption, which is very important, in particular, in mobile applications (displays for mobile phones, pagers, PDAs, etc.) which are reliant on rechargeable and standard batteries. Conversely, greater brightnesses are obtained for the same energy consumption, which may be interesting, for example, for illumination applications.
(2) It has furthermore surprisingly been found that, again in direct comparison, the polymers according to the invention have longer operating lifetimes, in particular in the case of green- and blue-emitting PLEDs.
(3) The accessibility and achievability of colours is the same or better in the case of the polymers according to the invention compared with the prior art. In particular in the case of blue-emitting polymers, an improved colour location and a more saturated blue emission is observed.

(4) Even without the use of electron-conducting comonomers, the polymers according to the invention are good electron conductors. Electron-conducting properties in polymers have hitherto been difficult to achieve since many electron conductors in accordance with the prior art are not sufficiently stable for high-quality applications.

(5) Since the novel polymer backbone of the formula (1) itself results in dark-blue emission, it is readily possible to introduce emitting units which still result in blue emission in the polymer. This makes it readily possible to separate charge-transport and emission properties in the polymer. Without wishing to be tied to a certain theory, we believe that this is necessary in order to obtain stable polymers. However, this was hitherto only possible with difficulty since the polymer backbone has itself always also emitted at the same time.

The present application text and also the examples below are directed to the use of polymers or blends according to the invention in relation to PLEDs and the corresponding displays. In spite of this restriction of the description, it is possible for the person skilled in the art, without further inventive step, also to use the polymers according to the invention for further uses in other electronic devices, for example for organic integrated circuits (O-ICs), organic field-effect transistors (O-FETs), organic thin-film transistors (O-TFTs), organic solar cells (O-SCs), organic field-quench devices (O-FQDs) or also organic laser diodes (O-lasers), to mention but a few applications.

The present invention likewise relates to the use of polymers according to the invention in the corresponding devices and to these devices themselves.

The comments made can furthermore likewise be applied to corresponding oligomers or dendrimers. The present invention likewise relates thereto.

The invention is explained in greater detail by the following examples without wishing to be restricted thereto.

EXAMPLE

Example 1

Synthesis of 2,7-dibromo-9,10-dimethylphenanthrene (monomer EM1 According to the Invention)

a) Synthesis of 2,7-dibromo-9,10-dihydroxy-9,10-dimethyl-9,10-dihydrophenanthrene

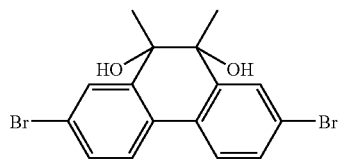

34.3 g (94 mmol) of 2,7-dibromophenanthrene-9,10-quinone were suspended in 600 ml of dry THF at −10° C. under argon, and 141 ml (282 mmol) of methylmagnesium chloride (2 molar solution in THF) were added dropwise at such a rate that the internal temperature did not exceed 0° C. The mixture was subsequently stirred overnight at room temperature. 50 ml of glacial acetic acid were added to the batch with ice cooling, and the mixture was diluted with ethyl acetate. After washing twice with saturated sodium chloride solution, the mixture was dried over sodium sulfate, and the solvents were removed, giving 43.4 g of the product, which was employed without further purification for the next step.

$^1$H-NMR (CDCl$_3$): [ppm] 7.84 (d, $^4J_{HH}$=2.0 Hz, 2H), 7.52 (d, $^3J_{HH}$=8.0 Hz, 2H), 7.46 (dd, $^4J_{HH}$=2.0 Hz, $^3J_{HH}$=8.4 Hz, 2H), 2.10 (s, exchangeable with D$_2$O, 2H, OH), 1.30 (s, 6H).

b) Synthesis of 2,7-dibromo-9-keto-10,10-dimethyl-9,10-dihydrophenanthrene

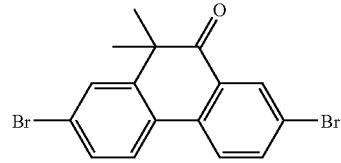

132.8 g (294 mmol) of 2,7-dibromo-9,10-dihydroxy-9,10-dimethyl-9,10-dihydrophenanthrene were suspended in 420 ml of acetic acid and 210 ml of trifluoroacetic acid under argon, and the mixture was stirred for 3 h under reflux. After the mixture had been stirred overnight at room temperature, it was filtered with suction, the residue was washed with water and methanol and dissolved in toluene, the solution was filtered through silica gel, and the solvent was removed, giving 89.9 g (80.4% of theory) of the product, which was used without further purification.

$^1$H-NMR (CDCl$_3$): [ppm] 8.17 (d, $^4J_{HH}$=2.4 Hz, 1H), 7.77 (m, 3H), 7.63 (d, $^4J_{HH}$=2.0 Hz, 1 H), 7.48 (dd, $^3J_{HH}$=8.4 Hz, $^4J_{HH}$=2.0 Hz,1H), 1.53 (s, 6H).

c) Synthesis of 2,7-dibromo-9-hydroxy-10,10-dimethyl-9,10-dihydrophenanthrene

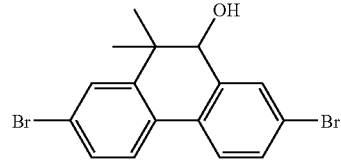

2.16 g (57 mmol) of lithium aluminium hydride were introduced into a flask which had been dried by heating. 100 ml of THF were added with ice-cooling. 43.4 g (114 mmol) of 2,7-dibromo-9-keto-10,10-dimethyl-9,10-dihydrophenanthrene in 150 ml of THF were then added dropwise, and the mixture was subsequently heated under reflux. The mixture was allowed to cool to room temperature overnight, 2 ml of H$_2$O were then carefully added. After the mixture had been stirred for 15 min, 2 ml of 15% NaOH were added, the mixture was stirred for 15 min, 6 ml of H$_2$O were added dropwise, and the mixture was stirred for 15 min. The resultant solid was filtered off with suction and washed with THF, and the solvent was removed from the filtrate, giving 43.4 9 of the product, which was employed without further purification.

$^1$H-NMR (DMSO-d$_6$): [ppm] 7.77 (m, 2H), 7.64 (d, $^4J_{HH}$=1.7 Hz,1H), 7.56 (d, $^4J_{HH}$=2.0 Hz, 1H), 7.50 (m, 2H), 5.62 (d, $^3J_{HH}$=5.0 Hz, 1H), 4.35 (d, exchangeable with D$_2$O, $^3J_{HH}$=5.0 Hz, 1H), 1.23 (s, 3H), 1.03 (s, 3H).

d) Synthesis of 2,7-dibromo-9,10-dimethylphenanthrene (EM1)

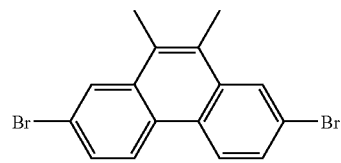

43.4 g (113 mmol) of 2,7-dibromo-9-hydroxy-10,10-dimethyl-9,10-dihydrophenanthrene were suspended in 610 ml of acetic acid. 780 mg of iodine and 3.5 ml of HBr in acetic acid were added, and the suspension was heated to reflux. The mixture was allowed to cool overnight with stirring. The residue was filtered off with suction and washed with water and methanol, giving 35.8 g (87.0% of theory) of the product.

$^1$H-NMR (CDCl$_3$): [ppm] 8.46 (d, $^3J_{HH}$=8.7 Hz, 2H), 8.21 (d, $^4J_{HH}$=1.7 Hz, 2H), 7.68 (dd, $^3J_{HH}$=8.7 Hz, $^4J_{HH}$=1.7 Hz, 2H), 2.67 (s, 6H).

Example 2

Synthesis of 2,7-dibromo-9,10-bis(2-ethylhexyl)phenanthrene (monomer EM2 According to the Invention)

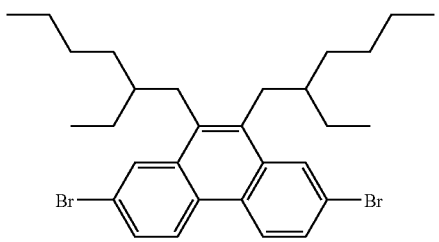

The synthesis was carried out analogously to Example 1 using 2-ethylhexylmagnesium chloride instead of methylmagnesium chloride.

$^1$H-NMR (CDCl$_3$): [ppm] 8.48 (d, $^3J_{HH}$=8.7 Hz, 2H), 8.25 (d, $^4J_{HH}$=1.3 Hz, 2H), 7.67 (dd, $^3J_{HH}$=9.0 Hz, $^4J_{HH}$=1.7 Hz, 2H), 3.11 (m, 4H), 1.68 (m, 2H), 1.26 (m, 16H), 0.88 (m, 12H).

Example 3

Synthesis of 2,7-dibromo-9,10-bis(4-tert-butylphenyl)phenanthrene (monomer EM3 According to the Invention)

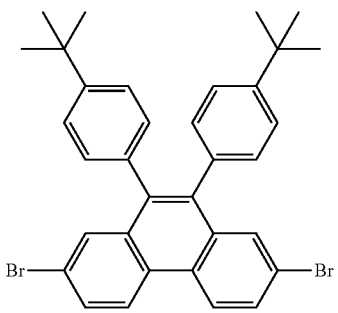

The synthesis was carried out analogously to Example 1 using 4-tert-butylphenylmagnesium chloride instead of methylmagnesium chloride. The product was purified by repeated recrystallization from toluene and from chlorobenzene.

$^1$H-NMR (CDCl$_3$): [ppm] 8.57 (d, $^3J_{HH}$=9.0 Hz, 2H), 7.84 (d, $^4J_{HH}$=2.0 Hz, 2H), 7.73 (dd, $^3J_{HH}$=9.0 Hz, $^4J_{HH}$=2.0 Hz, 2H), 7.18 (d, $^3J_{HH}$=8.4 Hz, 4H), 7.18 (d, $^3J_{HH}$=8.7 Hz, 4H), 1.27 (s, 18H).

Example 4

Synthesis of 2,7-dibromo-9,10-bis(n-octyl)phenanthrene (monomer EM4 According to the Invention)

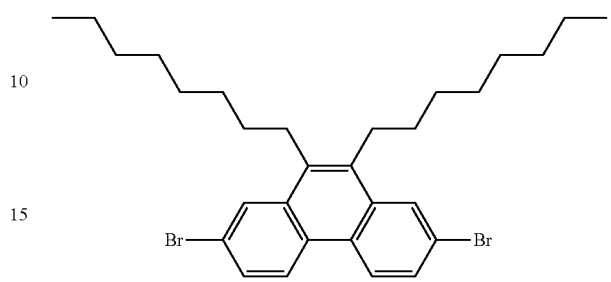

The synthesis was carried out analogously to Example 1 using a Grignard reagent made from 1-octyl bromide instead of methylmagnesium chloride. The product was purified by repeated recrystallization from MeOH/acetone.

$^1$H-NMR (CDCl$_3$): [ppm] 8.48 (d, $^3J_{HH}$=9.0 Hz, 2H), 8.18 (d, $^4J_{HH}$=2.0 Hz, 2H), 7.67 (dd, $^3J_{HH}$=9.0 Hz, $^4J_{HH}$=2.0 Hz, 2H), 3.01 (m, 4H), 1.66 (m, 4H), 1.54 (m, 4H), 1.43 (m, 4H), 1.32 (m, 12H), 0.91 (t, $^3J_{HH}$=7.0 Hz, 6H).

Example 5

Synthesis of 2,7-bis(ethylene glycol borate)-9,10-bis(n-octyl)phenanthrene (monomer EM5 According to the Invention)

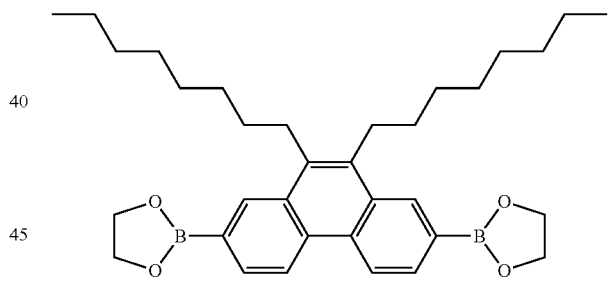

The solution of the Grignard reagent prepared from 34.4 g (61.4 mmol) of EM4 and 3.14 g (129.1 mmol) in 200 ml of dry THF was added dropwise at −75° C. to a solution of 20.6 ml (184.2 mmol) of trimethyl borate in 70 ml of dry THF, the mixture was stirred for 3 h at −75° C. and then brought to room temperature. The suspension was diluted with ethyl acetate, 10 ml of glacial acetic acid and water, the organic phase was separated off, washed twice with water and dried over sodium sulfate, and the solvent was removed. The solid which remained was suspended in toluene, 6.8 ml (368.4 mmol) of anhydrous ethylene glycol were added, and the suspension was heated at a vigorous boil for 2 h on a water separator. The solvent was removed again, and the residue was recrystallized from ethyl acetate to a purity of 99.9%.

$^1$H-NMR (CDCl$_3$): [ppm] 8.74 (d, $^3J_{HH}$=9.0 Hz, 2H), 8.62 (d, $^4J_{HH}$=2.0 Hz,2H), 7.97 (dd, $^3J_{HH}$=9.0 Hz, $^4J_{HH}$=2.0 Hz, 2H), 4.46 (s, 8H), 3.20 (m, 4H), 1.72 (m, 4H), 1.59 (m, 4H), 1.44 (m, 4H), 1.32 (m, 12H), 0.91 (t, $^3J_{HH}$=7.0 Hz, 6H).

Example 6

Synthesis of N,N'-bis(4-bromophenyl)-N,N'-bis(4-tert-butylphenyl)-9,10-dimethylphenanthrene-2,7-diamine (monomer EM6 According to the Invention)

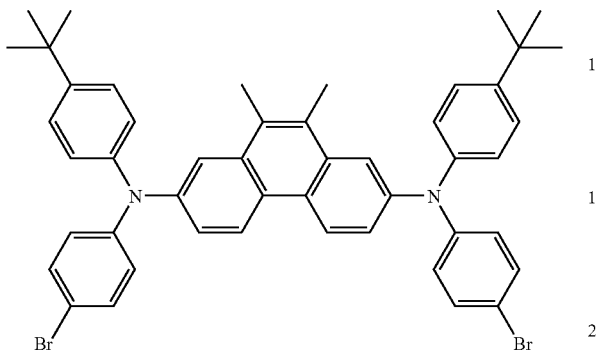

a) N,N'-Diphenyl-N,N'-bis(4-tert-butylphenyl)-9,10-dimethylphenanthrene-2,7-diamine A degassed solution of 30.75 g (84.5 mmol) of 2,7-dibromo-9,10-dimethylphenanthrene and 36.0 g (162 mmol) of 4-tert-butylphenylphenylamine (synthesised as described in *J. Org. Chem.* 2003, 68, 452) in 250 ml of toluene was saturated with $N_2$ for 1 h. Firstly 313 mg (1.55 mmol) of $P(^tBu)_3$, then 173 mg (0.76 mmol) of $Pd(OAc)_2$ were then added to the solution; 9.7 g (101 mmol) of $NaO^tBu$ in the solid state were subsequently added. The reaction mixture was heated under reflux for 5 h. After cooling to room temperature, 1.4 g of NaCN and 70 ml of water were carefully added. The organic phase was washed with 4×100 ml of $H_2O$, dried over $MgSO_4$, and the solvents were removed under reduced pressure. Chromatographic purification over silica gel gave a yellow oil. The yield—at a purity of 99.2% according to HPLC—was 59 g (99% of theory). $^1$H-NMR (DMSO-$d_6$, 500 MHz): 1.33 (s, 18H), 2.34 (s, 6H), 6.97-7.89 (m, 10H), 7.95 (d, J=8.36 Hz, 2H), 7.25 (d, J=8.7 Hz, 2H), 7.30 (t, J=7.7 Hz, 4H), 7.36 (d, J=8.7 Hz, 4H), 7.59 (d, J=2.3 Hz, 2H).

b) N,N'-bis(4-Bromophenyl)-N,N'-bis(4-tert-butylphenyl)-9,10-dimethylphenanthrene-2,7-diamine (EM6)

30 g (54.9 mmol) of N,N'-diphenyl-N,N'-bis(4-tert-butylphenyl)-9,10-dimethylphenanthrene-2,7-diamine were initially introduced in 600 ml of THF. A solution of 19.03 g (106.0 mmol) of NBS, dissolved in 400 ml of THF, was subsequently added dropwise at 0° C. with exclusion of light, the mixture was allowed to come to room temperature and was stirred for a further 4 h. 600 ml of water were subsequently added to the mixture, and the mixture was extracted with $CH_2Cl_2$. The organic phase was dried over $MgSO_4$, and the solvents were removed under reduced pressure. The product was washed by stirring with hot hexane and filtered off with suction, giving 35.1 g (94.3% of theory) of a colourless solid, which, after repeated recrystallization from ethyl acetate, had an HPLC purity of 99.9%.

$^1$H-NMR (DMSO-$d_6$, 500 MHz): 1.30 (s, 18H), 2.51 (s, 6H), 6.85 (d, J=8.7 Hz, 2H), 6.96 (d, J=8.7 Hz, 3H), 7.09 (d, J=8.7 hz, 3H), 7.25 (d, J=8.76 Hz, 2H), 7.39 (d, J=8.7 Hz, 4H), 7.45 (d, J=8.7 Hz, 4H), 7.68 (m, 2H), 8.61 (d, J=8.8 Hz, 2H).

Example 7

Synthesis of N,N'-bis(4-bromophenyl)-N,N'-bis(4-tert-butylphenyl)-9,10-bis(n-octyl)phenanthrene-2,7-diamine (monomer EM7 According to the Invention)

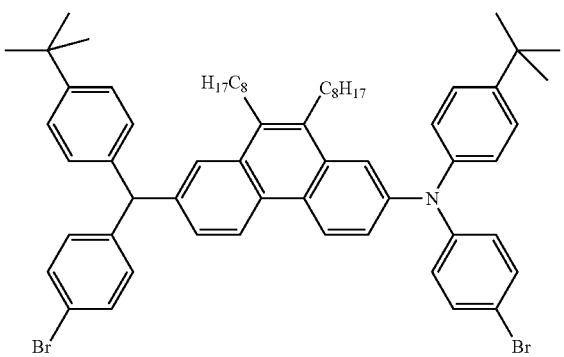

a) N,N'-Diphenyl-N,N'-bis(4-tert-butylphenyl)-9,10-bis(n-octyl)phenanthrene-2,7-diamine The synthesis was carried out analogously to Example 6a), where the starting material employed was 47.3 g (84.5 mmol) of 2,7-dibromo-9,10-bis(n-octyl)phenanthrene. Chromatographic purification over silica gel gave a yellow oil. The yield—at a purity of 99.2% according to HPLC—was 50 g (91% of theory).

$^1$H-NMR (DMSO-$d_6$, 500 MHz): 0.91 (t, J=6.7 Hz, 6H), 1.34 (s, 18H), 1.36-1.45 (m, 12H), 1.47 (m, 4H), 1.58 (m, 4H), 1.69 (m, 4H), 3.09 (t, J=8.3 Hz, 4H), 6.96-7.88 (m, 10H), 7.96 (d, J=8.35 Hz, 2H), 7.23 (d, J=8.7 Hz, 2H), 7.30 (t, J=7.7 Hz, 4H), 7.36 (d, J=8.7 Hz, 4H), 7.59 (d, J=2.3 Hz, 2H).

b) N,N'-bis(4-Bromophenyl)-N,N'-bis(4-teit-butylphenyl)-9,10-bis(n-octyl)phenanthrene-2,7-diamine (EM7)

The synthesis was carried out analogously to Example 6b), where the starting material employed was 55.3 g (54.9 mmol) of N,N'-diphenyl-N,N'-bis(4-tert-butylphenyl)-9,10-bis(n-octyl)phenanthrene-2,7-diamine. 76.1 g (90.3% of theory) of a colourless solid were obtained which, after repeated recrystallization from ethyl acetate, had an HPLC purity of 99.9%.

$^1$H-NMR (DMSO-$d_6$, 500 MHz): 0.92 (t, J=6.7 Hz, 6H), 1.33 (s, 18H), 1.36-1.45 (m, 12H), 1.48 (m, 4H), 1.58 (m, 4H), 1.70 (m, 4H), 3.10 (t, J=8.3 Hz, 4H), 6.85 (d, J=8.7 Hz, 2H), 6.96 (d, J=8.7 Hz, 3H), 7.09 (d, J=8.7 Hz, 3H), 7.25 (d, J=8.76 Hz, 2H), 7.39 (d, J=8.7 Hz, 4H), 7.45 (d, J=8.7 Hz, 4H), 7.68 (m, 2H), 8.61 (d, J=8.8 Hz, 2H)

Example 8

2,7-Bis[2-(4-Bromophenyl)vinyl]-9,10-dioctylphenanthrene (monomer EM8 According to the Invention)

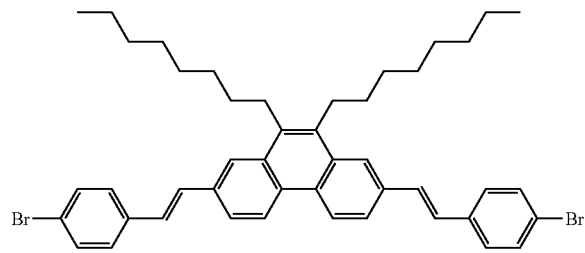

The preparation was carried out starting from EM4 by preparation of a Grignard reagent analogously to the preparation of EM5 and subsequent reaction with 10 equivalents of DMF. After acidic work-up, extraction and removal of the solvent, the aldehyde obtained was, after characterization by $^1$H-NMR, converted into the distilbene without further purification: 10.7 g (35 mmol) of diethyl (4-bromobenzyl)phosphonate were dissolved in 100 ml of dry DMF, 6.7 g (70 mmol) of NaO$^t$Bu were added at about 5° C. under a protective gas, after a stirring time of 30 min. at 5° C. the phenanthrene bisaldehyde (7.3 g, 159 mmol) was added at max. 5° C., and the mixture was subsequently stirred for 1 h at 5° C. For work-up, 20 ml of 4 M HCl and 50 ml of MeOH were added dropwise, the resultant precipitate was filtered off with suction and recrystallized from toluene to a purity of 99.8%.

$^1$H-NMR (CDCl$_3$): [ppm] 8.64 (d, $^3J_{HH}$=9.0 Hz, 2H), 8.29 (d, $^4J_{HH}$=1.0 Hz, 2H), 7.77 (dd, $^3J_{HH}$=9.0 Hz, $^4J_{HH}$=1.0 Hz, 2H), 7.33 (d, $^3J_{HH}$=8.4 Hz, 4H), 7.25 (d, $^3J_{HH}$=16 Hz, 2H), 7.11 (d, $^3J_{HH}$=16 Hz, 2H), 7.03 (d, $^3J_{HH}$=8.4 Hz, 4H), 3.25 (m, 4H), 1.75 (m, 4H), 1.62 (m, 4H), 1.45 (m, 4H), 1.32 (m, 12H), 0.91 (t, $^3J_{HH}$=7.0 Hz, 6H).

Example 9

Polymers P1 to P3 and Comparative Polymer C1

The polymers were synthesised as described in WO 03/048225. The further monomers used (apart from those already mentioned above) are shown below:

M1

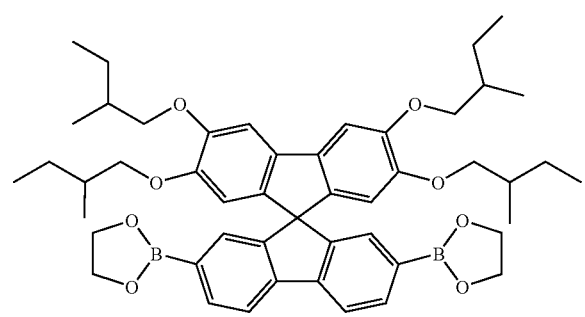

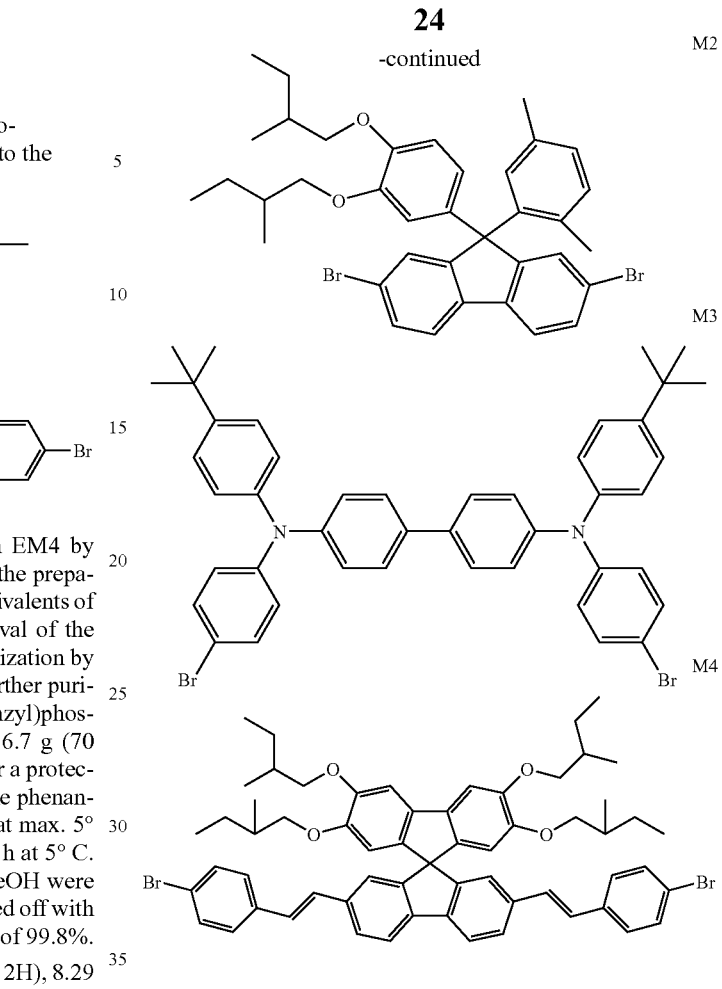

PLEDs were constructed using all polymers (in accordance with the general procedure as described in WO 04/037887). The composition of the polymers and the results of the electroluminescence measurements are shown in Table 1:

TABLE 1

EL data of some polymers according to the invention and of a comparative polymer (the efficiency here stands for the maximum efficiency, the voltage is the voltage required for a brightness of 100 cd/m², and the colour is indicated in CIE x/y coordinates).

| Polymer | Composition | Efficiency | Voltage | Colour |
|---------|-------------|------------|---------|--------|
| P1 | 50% M1, 30% M2, 10% M4, 10% EM6 | 4.1 cd/A | 3.7 V | 0.16/0.26 |
| P2 | 50% M1, 30% M2, 10% EM8, 10% M3 | 4.1 cd/A | 4.0 V | 0.18/0.28 |
| P3 | 50% M1, 30% M2, 10% EM8, 10% EM6 | 4.1 cd/A | 4.1 V | 0.19/0.31 |
| C1 | 50% M1, 30% M2, 10% M4, 10% M3 | 4.1 cd/A | 4.4 V | 0.19/0.33 |

All polymers exhibited blue luminescence with comparable efficiency. The voltage of the polymers according to the invention was lower here than for the comparative polymer in accordance with the prior art. In addition, the polymers according to the invention exhibited a darker-blue emission than the comparative polymer in accordance with the prior art and are thus more suitable for the application. The lifetime was about 5-10% higher in the case of P1 to P3 than in the case of C1.

Example 10

Polymer P4 and Comparative Polymer C1

Polymer P4 according to the invention comprises 50 mol % of EM5, 30 mol % of M2, 10 mol % of M3 and 10 mol % of M4. Comparative polymer C1 comprises monomer M1 instead of the monomer according to the invention. PLEDs were constructed using both polymers (in accordance with the general procedure as described in WO 04/037887). Polymer P4 according to the invention exhibited blue luminescence with an efficiency of 4.3 cd/A, the comparative polymer with an efficiency of 4.1 cd/A. Polymer P4 according to the invention required a voltage of 4.3 V for 100 cd/m², while a voltage of 4.4 V was required for the same brightness using comparative polymer C1. In addition, P4 (CIE x/y 0.18/0.30) exhibited a darker-blue emission than C1 (CIE x/y 0.19/0.33) and is thus more suitable for the application than the comparative polymer in accordance with the prior art. The lifetime was about 30% higher in the case of P4 than in the case of C1.

The invention claimed is:

1. Polymers containing at least 5 mol % of units of the formula (1)

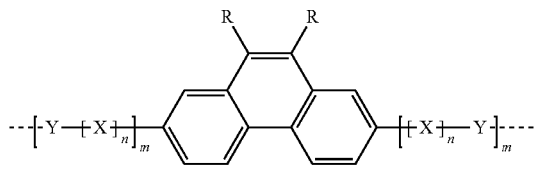

Formula (1)

where the symbols and indices used have the following meaning:

R is on each occurrence, identically or differently, H, a straight-chain, branched or cyclic alkyl chain having 1 to 40 C atoms, which may be substituted by $R^1$, and in which, in addition, one or more non-adjacent C atoms may be replaced by N—$R^1$, O, S, O—CO—O, CO—O, —$CR^1$=$CR^1$— or —C≡C—, with the proviso that the heteroatoms are not bonded directly to the phenanthrene unit, and in which, in addition, one or more H atoms may be replaced by F, Cl, Br, I or CN, or an aromatic or heteroaromatic ring system having 2 to 40 C atoms, which may also be substituted by one or more radicals $R^1$, or a combination of a plurality of these systems; the two radicals R here may also form a further mono- or polycyclic, aliphatic ring system with one another; with the proviso that at least one of the two radicals R is not equal to H;

X is on each occurrence, identically or differently, —$CR^1$=$CR^1$—, —C≡C— or N—Ar;

Y is on each occurrence, identically or differently, a divalent aromatic or heteroaromatic ring system having 2 to 40 C atoms, which may be substituted by one or more radicals $R^1$ or unsubstituted;

$R^1$ is on each occurrence, identically or differently, H, a straight-chain, branched or cyclic alkyl or alkoxy chain having 1 to 22 C atoms, in which, in addition, one or more non-adjacent C atoms may be replaced by N—$R^2$, O, S, O—CO—O, CO—O, —$CR^2$=$CR^2$—, —C≡C— and in which, in addition, one or more H atoms may be replaced by F, Cl, Br, I or CN, or an aryl, heteroaryl, aryloxy or heteroaryloxy group having 5 to 40 C atoms, which may also be substituted by one or more non-aromatic radicals $R^1$; two or more of the radicals $R^1$ here may also form a ring system with one another and/or with R; or F, Cl, Br, I, CN, N($R^2$)$_2$, Si($R^2$)$_3$ or B($R^2$)$_2$;

$R^2$ is on each occurrence, identically or differently, H or an aliphatic or aromatic hydrocarbon radical having 1 to 20 C atoms;

Ar is on each occurrence, identically or differently, a monovalent aromatic or heteroaromatic ring system having 2 to 40 C atoms, which may be substituted by $R^1$ or unsubstituted;

n is on each occurrence, identically or differently, 0 or 1;

m is on each occurrence, identically or differently, 0, 1 or 2;

the dashed bond here as denotes the link in the polymer;

it is not intended to represent a methyl group here;

wherein the further structural elements are used as backbone, selected from the classes of the 4,5-dihydropyrene derivatives, 4,5,9,10-tetrahydropyrene derivatives, fluorene derivatives, 9,9'-spirobifluorene derivatives, 9,10-dihydrophenanthrene derivatives, 5,7-di-hydrodibenzoxepine derivatives and cis- and trans-indenofluorene derivatives.

2. The polymer according to claim 1, wherein the polymers are conjugated or partially conjugated polymers.

3. The polymer according to claim 1, which additionally comprise further structural elements besides the units of the formula (1).

4. Polymers according to claim 3, wherein the further structural elements which increase the hole-injection and/or -transport properties are triarylamine, benzidine, tetraaryl-para-phenylenediamine, triarylphosphine, phenothiazine, phenoxazine, dihydrophenazine, thianthrene, dibenzo-p-dioxin, phenoxathiyne, carbazole, azulene, thiophene, pyrrole, furan derivatives or O—, S— or N-containing heterocycles having a high HOMO.

5. The polymer according to claim 3, wherein the further structural elements which increase the electron-injection and/or -transport properties are pyridine, pyrimidine, pyridazine, pyrazine, oxadiazole, quinoline, quinoxaline, benzothiadiazole, phenazine derivatives, triarylboranes or O—, S—or N-containing heterocycles having a low LUMO.

6. The polymer according to claim 4, wherein the further structural elements have combinations of individual units selected from the group consisting of triarylamine, benzidine, tetraaryl-para-phenylenediamine, triarylphosphine, phenothiazine, phenoxazine, dihydrophenazine, thianthrene, dibenzo-p-dioxin, phenoxathiyne, carbazole, azulene, thiophene, pyrrole, furan derivatives, O—, S—or N-containing heterocycles having a high HOMO, pyridine, pyrimidine, pyridazine, pyrazine, oxadiazole, quinoline, quinoxaline, benzothiadiazole, phenazine derivatives, triarylboranes or O—, S—and N-containing heterocycles having a low LUMO.

7. The polymer according to claim 3, wherein the further structural elements change the emission characteristics to such an extent that electrophosphorescence can be obtained instead of electrofluorescence.

8. The polymer according to claim 3, wherein the further structural elements improve the transition from the singlet state to the triplet state, selected from the classes of the carbazole and bridged carbazole dimer units, ketones, phosphine oxides, sulfoxides, sulfones and silane derivatives.

9. The polymer according to claim 3, wherein the further structural elements are 1,4-phenylene, 1,4-naphthylene, 1,4- or 9,10-anthrylene, 1,6- or 2,7- or 4,9-pyrenylene, 3,9-or 3,10- perylenylene, 4,4'-biphenylylene, 4,4''-terphenylylene, 4,4'-bi-1,1'-naphthylylene, 4,4'-tolanylene, 4,4'-stilbenylene or 4,4''-bisstyrylarylene derivatives.

10. The polymer according to claim 3, wherein the proportion of the units of the formula (1) is at least 10 mol %.

11. Polymers according to claim 1, wherein in addition to units of the formula (1), the polymers contain at least two structural units from selected from the group consisting of triarylamine, benzidine, tetraaryl-para-phenylenediamine, triarylphosphine, phenothiazine, phenoxazine, dihydrophenazine, thianthrene, dibenzo-p-dioxin, phenoxathiyne, carbazole, azulene, thiophene, pyrrole, furan derivatives, O—, S— or N-containing heterocycles having a high HOMO, pyridine, pyrimidine, pyridazine, pyrazine, oxadiazole, quinoline, quinoxaline, benzothiadiazole, phenazine derivatives, triarylboranes, O—, S— or N-containing heterocycles having a low LUMO, carbazole and bridged carbazole dimer units, ketones, phosphine oxides, sulfoxides, sulfones, silane derivatives, 1,4-phenylene, 1,4-naphthylene, 1,4- or 9,10-anthrylene, 1,6- or 2,7- or 4,9-pyrenylene, 3,9- or 3,10-perylenylene, 4,4'-biphenylylene, 4,4"-terphenylylene, 4,4'-bi-1,1'-naphthylylene, 4,4'-tolanylene, 4,4'-stilbenylene or 4,4"-bisstyrylarylene derivatives 4,5-dihydropyrene derivatives, 4,5,9,10-tetrahydropyrene derivatives, fluorene derivatives, 9,9'-spirobifluorene derivatives, 9,10-dihydrophenanthrene derivatives, 5,7-dihydrodibenzoxepine derivatives and cis- and trans-indenofluorene derivatives.

12. The polymer according to claim 11, characterised in that one of these structural units is selected from the group of the hole-conducting units and the other group is an emitting unit.

13. Polymers according to claim 1, wherein the symbol R, identically or differently on each occurrence, stands for a straight-chain, branched or cyclic alkyl chain having 2 to 15 C atoms, in which, in addition, one or more non-adjacent C atoms may be replaced by N—$R^1$, O, S, O—CO—O, CO—O, —CH=CH— or —C≡C—, with the proviso that the heteroatoms are not bonded directly to the phenanthrene unit, and in which, in addition, one or more H atoms may be replaced by F or CN, or an aromatic or heteroaromatic group having 4 to 20 C atoms, which may also be substituted by one or more non-aromatic radicals $R^1$, or a combination of a plurality of these systems; the two radicals R here may together also form a further mono- or polycyclic, aromatic or aliphatic ring system.

14. Polymers according to claim 1, wherein the symbol X, identically or differently on each occurrence, stands for —CH=CH—, —C≡C— or N—Ar.

15. The polymer according to claim 1, wherein the symbol Y, identically or differently on each occurrence, stands for a divalent aromatic or heteroaromatic ring system having 4 to 25 C atoms, which may be substituted by one or more radicals $R^1$.

16. A polymer containing at least 5 mol % of units of the formula (1)

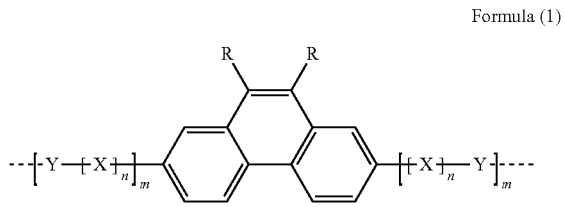

Formula (1)

where the symbols and indices used have the following meaning:

R is on each occurrence, identically or differently, H, a straight-chain, branched or cyclic alkyl chain having 1 to 40 C atoms, which may be substituted by $R^1$, and in which, in addition, one or more non-adjacent C atoms may be replaced by N—$R^1$, O, S, O—CO—O, CO—O, —$CR^1$=$CR^1$— or —C≡C—, with the proviso that the heteroatoms are not bonded directly to the phenanthrene unit, and in which, in addition, one or more H atoms may be replaced by F, Cl, Br, I or CN, or an aromatic or heteroaromatic ring system having 2 to 40 C atoms, which may also be substituted by one or more radicals $R^1$, or a combination of a plurality of these systems; the two radicals R here may also form a further mono- or polycyclic, aliphatic ring system with one another; with the proviso that at least one of the two radicals R is not equal to H;

X is on each occurrence, identically or differently, —$CR^1$=$CR^1$—, —C≡C— or N—Ar;

Y is on each occurrence, identically or differently, a divalent aromatic or heteroaromatic ring system having 2 to 40 C atoms, which may be substituted by one or more radicals $R^1$ or unsubstituted;

$R^1$ is on each occurrence, identically or differently, H, a straight-chain, branched or cyclic alkyl or alkoxy chain having 1 to 22 C atoms, in which, in addition, one or more non-adjacent C atoms may be replaced by N—$R^2$, O, S, O—CO—O, CO—O, —$CR^2$=$CR^2$—, —C≡C— and in which, in addition, one or more H atoms may be replaced by F, Cl, Br, I or CN, or an aryl, heteroaryl, aryloxy or heteroaryloxy group having 5 to 40 C atoms, which may also be substituted by one or more non-aromatic radicals $R^1$; two or more of the radicals $R^1$ here may also form a ring system with one another and/or with R; or F, Cl, Br, I, CN, N$(R^2)_2$, Si$(R^2)_3$ or B$(R^2)_2$;

$R^2$ is on each occurrence, identically or differently, H or an aliphatic or aromatic hydro-carbon radical having 1 to 20 C atoms;

Ar identically or differently on each occurrence stands for a monovalent aromatic or heteroaromatic ring system having 4 to 25 C atoms, which may be substituted by $R^1$ or unsubstituted;

n is on each occurrence, identically or differently, 0 or 1;

m is on each occurrence, identically or differently, 0, 1 or 2;

the dashed bond here as denotes the link in the polymer;

it is not intended to represent a methyl group here, and wherein the polymer has 10 to 10.000 recurring units.

17. The polymer according to claim 1, wherein the index m, identically or differently on each occurrence, stands for 0 or 1.

18. The polymer according to claim 1, wherein the polymer contains units of the formula (1) as backbone, and n is on each occurrence equal to 0.

19. A polymer containing at least 5 mol % of units of the formula (1)

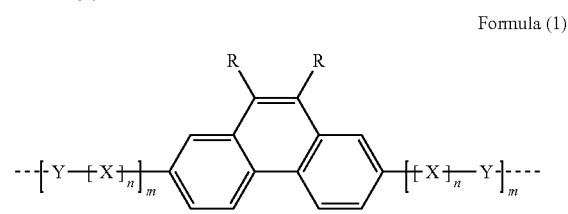

Formula (1)

where the symbols and indices used have the following meaning:

R is on each occurrence, identically or differently, H, a straight-chain, branched or cyclic alkyl chain having 1 to 40 C atoms, which may be substituted by $R^1$, and in which, in addition, one or more non-adjacent C atoms may be replaced by N—R$^1$, O, S, O—CO—O, CO—O, —CR$^1$=CR$^1$— or —C≡C—, with the proviso that the heteroatoms are not bonded directly to the phenanthrene unit, and in which, in addition, one or more H atoms may be replaced by F, Cl, Br, I or CN, or an aromatic or heteroaromatic ring system having 2 to 40 C atoms, which may also be substituted by one or more radicals R$^1$, or a combination of a plurality of these systems; the two radicals R here may also form a further mono- or polycyclic, aliphatic ring system with one another; with the proviso that at least one of the two radicals R is not equal to H;

X is on each occurrence, identically or differently, N—Ar;

Y is on each occurrence, identically or differently, a divalent aromatic or heteroaromatic ring system having 2 to 40 C atoms, which may be substituted by one or more radicals R$^1$ or unsubstituted;

R$^1$ is on each occurrence, identically or differently, H, a straight-chain, branched or cyclic alkyl or alkoxy chain having 1 to 22 C atoms, in which, in addition, one or more non-adjacent C atoms may be replaced by N—R$^2$, O, S, O—CO—O, CO—O, —CR$^2$=CR$^2$—, —C≡C— and in which, in addition, one or more H atoms may be replaced by F, Cl, Br, I or CN, or an aryl, heteroaryl, aryloxy or heteroaryloxy group having 5 to 40 C atoms, which may also be substituted by one or more non-aromatic radicals R$^1$; two or more of the radicals R$^1$ here may also form a ring system with one another and/or with R; or F, Cl, Br, I, CN, N(R$^2$)$_2$, Si(R$^2$)$_3$ or B(R$^2$)$_2$;

R$^2$ is on each occurrence, identically or differently, H or an aliphatic or aromatic hydro-carbon radical having 1 to 20 C atoms;

Ar is on each occurrence, identically or differently, a monovalent aromatic or heteroaromatic ring system having 2 to 40 C atoms, which may be substituted by R$^1$ or unsubstituted;

n is on each occurrence, identically or differently, 0 or 1;

m is on each occurrence, identically or differently, 0, 1 or 2;
  the dashed bond here as denotes the link in the polymer;
    it is not intended to represent a methyl group here,
wherein the polymer contains units of the formula (1) as hole-transporting units, and n is on each occurrence, identically or differently, 0 or 1, where at least one n =1;

m is on each occurrence, identically or differently, 0, 1 or 2, where m is not equal to 0 if the corresponding n=1.

20. The polymer according to claim 1, wherein the polymer contains units of the formula (1) as emitters, and n is on each occurrence, identically or differently, 0 or 1, where at least one n=1;

m is on each occurrence, identically or differently, 0, 1 or 2, where m is not equal to 0 if the corresponding n=1; and X is on each occurrence, identically or differently, —CR$^1$=CR$^1$—, —C≡C—or N—Ar, where at least one X is equal to —CR$^1$=CR$^1$—or —C≡C—.

21. The polymer according to claim 1, wherein the units of the formula (1) are symmetrically substituted in the 9,10-positions of the phenanthrene units.

22. The polymer according to claim 1, wherein the polymer is prepared by SUZUKI polymerisation, YAMAMOTO polymerisation, STILLE polymerisation or HARTWIG-BUCHWALD polymerisation.

23. Mixtures (blends) of one or more polymers according to claim 1 with further polymeric, oligomeric, dendritic or low-molecular-weight substances.

24. An organic electronic component having one or more active layers, characterised in that at least one of these active layers comprises one or more polymers or blends according to claim 1.

25. The organic electronic component according to claim 24, characterised in that it is polymeric light-emitting diodes (PLEDs), organic integrated circuits (O-ICs), organic field-effect transistors (O-FETs), organic thin-film transistors (O-TFTs), organic solar cells (O-SCs), organic field-quench devices (O-FQDs) or organic laser diodes (O-lasers).

26. The organic electronic component according to claim 25, characterised in that it is a polymeric light-emitting diode.

27. The polymer according to claim 3, wherein the proportion of the units of the formula (1) is at least 30 mol %.

28. The polymer according to claim 3, wherein the proportion of the units of the formula (1) is at least 50 mol %.

29. The polymer as claimed in claim 16, wherein the polymer further comprises further structural units.

30. The polymer as claimed in claim 29, wherein the further structural units may originate from the classes described below:
  Group 1: Units which increase the hole-injection and/or -transport properties of the polymers;
  Group 2: Units which increase the electron-injection and/or -transport properties of the polymers;
  Group 3: Units which have combinations of individual units from group 1 and group 2;
  Group 4: Units which change the emission characteristics to such an extent that electrophosphorescence instead of electrofluorescence may be obtained;
  Group 5: Units which improve the transition from the singlet state to the triplet state;
  Group 6: Units which influence the morphology or also the emission colour of the resultant polymers; and
  Group 7: Units which are used as a backbone.

31. The polymer as claimed in claim 16, wherein the polymer has between 50 to 5000 recurring units.

32. The polymer as claimed in claim 16, wherein the polymer has between 50 to 2000 recurring units.

33. The polymer according to claim 16, wherein the proportion of the units of the formula (1) is at least 30 mol %.

34. The polymer according to claim 16, wherein the proportion of the units of the formula (1) is at least 50 mol %.

* * * * *